(12) United States Patent
Augenstein

(10) Patent No.: US 8,865,453 B2
(45) Date of Patent: Oct. 21, 2014

(54) LANDFILL BIOFILTRATION SYSTEM AND METHODS FOR REMOVAL OF GAS-PHASE POLLUTANTS AND CONTAMINANTS

(75) Inventor: Don C. Augenstein, Palo Alto, CA (US)

(73) Assignee: Intititute For Environmental Management, Palo Alto, CA (US)

( * ) Notice: Subject to any disclaimer, the term of this patent is extended or adjusted under 35 U.S.C. 154(b) by 2116 days.

(21) Appl. No.: 11/975,234

(22) Filed: Oct. 18, 2007

(65) Prior Publication Data

US 2008/0044889 A1    Feb. 21, 2008

Related U.S. Application Data

(63) Continuation of application No. 10/138,617, filed on May 3, 2002, now abandoned.

(60) Provisional application No. 60/288,624, filed on May 3, 2001.

(51) Int. Cl.
     *B01D 53/56*      (2006.01)
     *B01D 53/85*      (2006.01)

(52) U.S. Cl.
     CPC .......... *B01D 53/85* (2013.01); *B01D 2257/502* (2013.01); *B01D 2257/302* (2013.01); *Y02C 20/10* (2013.01); *B01D 2257/402* (2013.01); *B01D 2257/404* (2013.01); *B01D 2257/708* (2013.01)
     USPC ..................... 435/266; 435/262.5; 435/299.1; 5/129.95

(58) Field of Classification Search
     USPC ................ 435/262, 262.5, 266, 299.1, 290.1; 210/603; 405/128.5, 129.25; 71/8–10
     See application file for complete search history.

(56) References Cited

U.S. PATENT DOCUMENTS

| | | | |
|---|---|---|---|
| 2,793,096 A | 5/1957 | Pomeroy | |
| 4,825,843 A * | 5/1989 | Novy | 123/585 |
| 5,066,392 A | 11/1991 | Kneer | |
| 5,463,165 A * | 10/1995 | Northrop | 588/250 |
| 5,503,738 A | 4/1996 | DeFilippi et al. | |
| 5,546,862 A | 8/1996 | Schabdach | |
| 5,795,751 A | 8/1998 | Apel | |
| 5,858,768 A | 1/1999 | Bonnin | |
| 5,888,022 A | 3/1999 | Green | |
| 6,013,512 A | 1/2000 | Turschmid et al. | |
| 6,024,513 A | 2/2000 | Hudgins et al. | |
| 6,056,800 A | 5/2000 | Carter | |
| 6,117,672 A | 9/2000 | Breckenridge | |
| 6,283,676 B1 | 9/2001 | Hater et al. | |

FOREIGN PATENT DOCUMENTS

| | | |
|---|---|---|
| EP | 429883 A2 | 6/1991 |
| JP | 06079129 A | 3/1994 |
| WO | WO 94/09885 | 5/1994 |
| WO | WO 9807974 A1 * | 2/1998 |

OTHER PUBLICATIONS

Hudepohl et al., "Biofilter Technology for NOx Control," Dept. of Civil & Environmental Engineering Univ. California Air Resources Board Research Div.

* cited by examiner

*Primary Examiner* — William H Beisner
(74) *Attorney, Agent, or Firm* — Hugh McTavish

(57) ABSTRACT

Biochemical decomposition of undesirable gaseous contaminants, including nitrogen oxides, VOC's, carbon monoxide and sulfur oxides, and malodorous contaminants, is achieved by passing a gas stream through a managed landfill providing microbiological activity capable of degrading the contaminants. Gases suitable for treatment include fuel combustor exhaust, landfill gases, putrescent gases and the like. The landfill functions as a biological reactor (bioreactor), where water is added if or as necessary to achieve concentrations between about 20% and about 65% by weight, and desired microbial contaminant abatement action. By a permeation of the polluted gas through the landfill, there is a consumption of polluting gases by microorganisms present in the landfill. The process enables increased combustion of fuels, such as landfill gases, whose energy values are currently wasted or are not available due to emissions problems. The excess oxygen normally present in exhaust can advantageously result in additional oxidative waste consumption by microorganisms, yielding additional "air space" that is an economic bonus in extending landfill life and/or lessening landfill use.

2 Claims, 3 Drawing Sheets

LANDFILL BIOFILTRATION SYSTEM AND METHODS FOR REMOVAL OF GAS-PHASE POLLUTANTS AND CONTAMINANTS

FIELD OF THE INVENTION

The field of the invention is the use of waste in landfills, and similar large tonnage waste masses such as large waste piles in dumps, in combination with appropriate landfill or waste dump management techniques, for removal of undesirable biodegradable noxious gases from emitted gas streams.

BACKGROUND OF THE INVENTION

The creation and emission of vapor-phase gas pollutants can be due to many human activities. For example, such pollutants can result from fuel combustion for energy, including fossil fuels, landfill gases and wood gasifier product gas. Combustion is also used for disposal of waste products which can be burned. Such waste products include gas from solid waste landfills (landfill gas), waste gas from oil refineries, and solid waste disposed of in incineration processes. Air streams or process exit gas can also commonly be contaminated with volatile organic compounds (VOC's), e.g. by cooking, fires, emissions of aerosols or their propellants, or putrescing wastes.

The combustion of fuels for energy, or burning of materials for disposal results in contaminants in product gas that include oxides of nitrogen, carbon monoxide, volatile organic compounds, and sulfur oxides. Among contaminants of regulatory concern are most often the three major oxides of nitrogen: nitrous oxide ($N_2O$), nitric oxide (NO) and nitrogen dioxide ($NO_2$) and, as well, carbon monoxide. As one example, U.S. emission limit standards commonly applied to natural gas firing are 0.06 pounds of NOx per one million Btu's and 0.2 pounds of CO (carbon monoxide) per million Btu's.

Internal combustion (IC, or piston) engines have a number of attractions, including their ability to use many fuels, such as landfill gas, and ready maintenance. But, despite their numerous advantages, such engines emit nitrogen oxides in amounts that are about five-fold those of other combustion-based mechanical and electrical power options. Depending on fuels and operations, IC Engines can also emit CO and unburned higher ($C_2^+$ [two-carbon] and up) hydrocarbons. Unburned higher hydrocarbons are then emitted as VOC's, which are regulated local air pollutants. In addition, the combustion of fuels containing sulfur can give rise to sulfur oxides ($SO_x$). Even as needs for various combustion processes increase in the US and worldwide, regulation and restriction of emissions, particularly $NO_x$, and CO, is becoming so stringent as to limit the use of these processes to far less than their full potential.

If these contaminant emissions could be reduced to meet regulatory standards (generally state or district-specific), or even better, eliminated, then the use of some combustion processes would be feasible both from economic, environmental and regulatory standpoints. For example, solid waste landfills generate combustible gas, which is undesirable if released into the atmosphere because of the presence of methane and higher hydrocarbon contaminants. However, if flue or exhaust gases resulting from landfill gas combustion can be appropriately cleaned, the landfill gas can be more readily used as a renewable fuel through its combustion in energy generating plants. This use not only abates pollutants, but can also reduce atmospheric emissions of landfill methane, a gas whose emissions are considered in the aggregate to have major adverse climate effects. Such landfill gas fuel use can conserve other fuels as well as reduce emission of fossil $CO_2$ from lessening use of fossil energy sources. For this reason, landfill gas energy use or abatement has substantial climate benefits. Benefits associated with energy use are such that the U.S. EPA encourages landfill gas use in its very active Landfill Methane Outreach Program (LMOP)

Using landfill gases or other energy sources for electricity generation at multiple smaller-scale sites near population centers, has become increasingly desirable, because it substantially lessens congestion and resultant resistance losses of electric power, especially in longer-distance electrical transmission lines. Such electricity fueling over multiple widespread facilities is termed "distributed generation". As noted, landfill gas combustion, whether for powering internal combustion engines or for use in other fuel combustors, can increase air pollutant emissions, particularly nitrogen oxides and carbon monoxide. Current emissions standards severely constrain use of landfill gas, in fueling such distributed generation. Thus methods for reduction or avoidance of emissions will be of high value.

Simultaneously, even as landfill gas energy use and distributed generation is emission constrained, landfill management technology is advancing concepts showing superior environmental benefits and potentials—including realization of much-increased landfill gas energy, if energy-related emissions were not barriers (Pacey et al. (1999) *The Bioreactor Landfill—An Innovation in Solid Waste Management*. Solid Waste Association of North America, Silver Spring, Md.)

The present Federal subtitle D landfill regulations evolved with the goal of keeping waste landfills dry. (This has, in the past decade, become known as the "Dry Entombment" approach). Alternative strategies have been recognized for some time and are now being rapidly developed. It is being shown that waste decomposition and methane generation can be accelerated and be better controlled by improving bacterial reaction conditions in "bioreactor" landfills (see, for example, Augenstein et al. (1976); Fuel Gas Recovery from Controlled Landfilling of Solid Wastes, Resources and Conservation, 1, 103-117; Barlaz et al. (1990); Methane Production from Municipal Refuse—A Review of Enhancement Techniques and Microbial Dynamics, Critical Reviews in Environmental Control, 19(6):557-584; Stessel et al. (1994) Design Implications of the in-Ground Digester, Proceedings, Air and Waste Management Association Meeting Cincinnati, June 19-24; Augenstein et al. (2000) Yolo County Controlled Landfill Project June, Proceedings, Second International Methane Mitigation Conference, Akademgorodok, Novosibirsk, Siberia, Russia. Proceedings available from US EPA. The bioreactor approach has a number of benefits as seen by landfill owner/operators and also regulators (see Pacey et al. (1999), supra.)

Yet other processes of numerous types are limited by emissions of pollutant or odorous compounds or both. There are a host of these processes, e.g. animal husbandry, confined animal operations, aerobic composting, forcing air through landfills for composting or heating purposes, and the like.

The present invention provides methods that reduce undesirable contaminating gases from combustion or landfill gas fueled generation, or polluted/odorous gases from other sources. A substantial source of renewable energy can be freed for economical use, and polluted exhaust gas or other gas streams can be cleaned at a relatively low cost.

Relevant Literature

Patents relating to bioremediation of gaseous pollutants include U.S. Pat. No. 5,503,738 (Apr. 2, 1996), which describes a process for remediating vaporous pollutants by passage through a bioreactor containing microorganisms capable of remediating the pollutants. U.S. Pat. No. 5,795,751 (Aug. 18, 1998) discloses a biofilter for reducing concentrations of gaseous nitrogen oxides in a polluted gas through an organic filter bed with denitrifying bacteria. U.S. Pat. No. 6,013,512 (Jan. 11, 2000) provides an apparatus for scrubbing gaseous emissions with simultaneous liquid scrubbing and biochemical decomposition of $NO_x$ or VOC or a combination thereof using an aqueous suspension held in a biomass chamber. U.S. Pat. No. 6,117,672 (Sep. 12, 2000) provides a system combining biomass filtration, anaerobic digestion, steam absorption refrigeration and heat exchangers wherein moist waste consumes the "nitrogenous oxides" in gases from a fuel combustor.

Other relevant work has been sponsored, for example by the California Air Resources Board, in (Hudepohl. N. J., Davidova, Y. du Plessis. C. Schroeder, E. D., and Chang, D. P. Y. 1999 *Biofilter Technology for NOx Control*. Department of Civil and Environmental Engineering, University of California, Davis). This uses a column reactor and nitrifying organisms to convert NO to $NO_2$, thence nitrate.

Patents relating to aerobic landfills include U.S. Pat. No. 5,546,862, relating to a method of landfill mining. U.S. Pat. No. 5,888,022 is directed to methods of improving aerobic degradation of the solid wastes emplaced in a landfill. U.S. Pat. No. 6,024,513 discloses improved methods of decomposing municipal solid wastes placed in a landfill.

SUMMARY OF THE INVENTION

Biochemical decomposition of undesirable contaminants of gases, including nitrogen oxides, VOC's, carbon monoxide and sulfur oxides, is achieved by passing a gas stream through a managed landfill providing microbiological activity capable of degrading the contaminants. Gases suitable for treatment include exhaust gases, landfill gas, odorous gases from putrefaction, and the like. In one preferred embodiment, the landfill is a bioreactor type, where liquid is added to achieve increased microbial action, and hence greater microbial activity in degrading both solid waste and gas contaminants. By permeating the polluted gas through the landfill, there is a consumption of polluting gases or vapors by microorganisms present in the landfill. The process enables increased combustion of fuels, such as landfill gas, that are currently wasted due to constraints on the pollutant emissions associated with their use, otherwise beneficially, as fuels for energy uses. In addition, the excess oxygen normally present in exhaust or flue gas can advantageously result in additional oxidative waste consumption by microorganisms, yielding additional "air space" that is an economic bonus in extending landfill life and/or lessening landfill use.

DETAILED DESCRIPTION OF THE EMBODIMENTS

Figure 1:
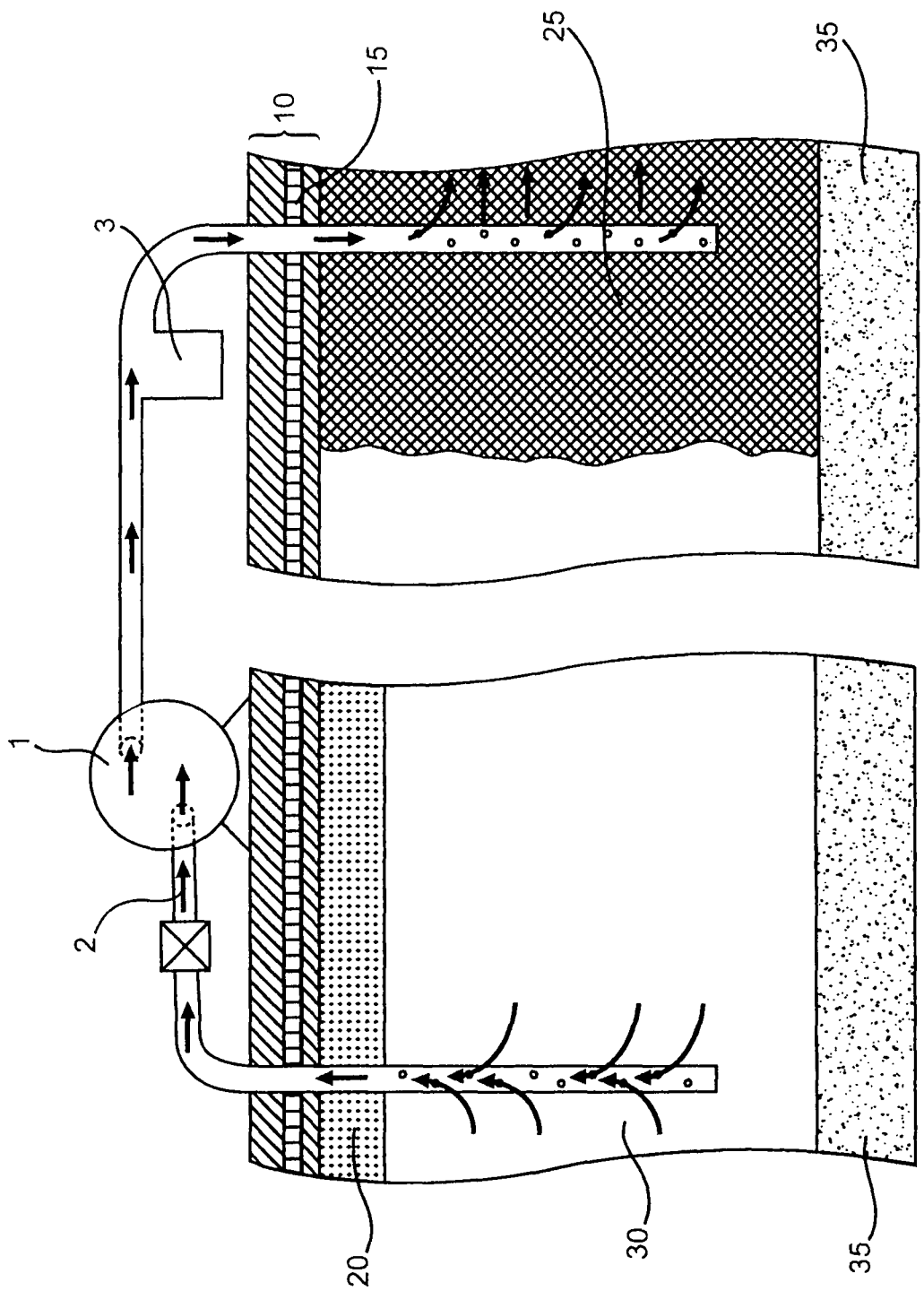
FIG. 1 is a schematic depicting the flow of gases into a landfill biofiltration system.

The present invention is drawn to methods and apparatus for removing polluting gases, including nitrogen oxides ($NO_x$), carbon monoxide, sulfur oxides ($SO_x$) and volatile organic compounds VOC's from a gas stream, by passing the gas stream through a landfill biofiltration system. Biologically mediated decomposition of these biodegradable gases takes place in the landfill, thereby permitting the subsequent release of the cleansed gases.

The use of an entire landfill or sectors thereof for a gas pollutant biofiltration system is advantageous over presently used biofilters for remediating or consuming gaseous pollutants. Presently used technologies require a substantial increased incremental investment in equipment and management that is not otherwise required. There are significant costs associated with emplacement and fabrication of equipment for purposes of biofiltration. There are additional costs associated with the maintenance and management of the biofilter constructed or fabricated solely for the purpose of gas cleanup, including addition of liquid, nutrients and possibly cleaning of that material that supports the bacteria ("support"). The area requirement ("footprint") and volume requirement can also be inconveniently large. The present invention provides a solution to these problems by utilizing a resource that is readily available, necessary in any event, and can be adapted so as to serve important functions as a biofilter, in addition to its normal waste disposal role.

The landfill or waste dump has the advantage of enormous size relative to any equipment that must ordinarily be constructed. This size provides a large surface area upon which the biological remediation reactions can take place, and very long residence times compared to those available in other bioremediation equipment.

Before the present device and method for removal of gaseous contaminants from polluted gases are disclosed and described, it is to be understood that this invention is not limited to the particular process steps and materials disclosed herein as such process steps and materials may vary somewhat. It is also to be understood that the terminology used herein is used for the purpose of describing particular embodiments only and is not intended to be limiting since the scope of the present invention will be limited only by the appended claims and functional equivalents thereof.

It must be noted that as used herein and in the appended claims, the singular forms "a", "an", and "the" include plural referents unless the context clearly dictates otherwise. Thus, for example, reference to "a gas" includes a plurality of such gases and reference to "the landfill" includes reference to one or more landfills and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the devices and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

Biofiltration.

As used herein refers to the venting and permeation of contaminated air, vapors, or gases through a biologically active material comprising microorganisms capable of metabolizing one or more of the polluting gases. A "biofilter" is a device containing a biologically active material or component through which contaminated gases, vapors, or air are vented for reducing amounts or concentrations of one or more contaminants or pollutants from the gases, vapors, or air. The biofilter of the present invention is a managed landfill, or alternately, waste dump of size comparable to a landfill. Such landfills are typically large masses, usually at least about 1 ton in landfill mass, more usually at least about 100 tons of mass, and may be at least about 1000 tons or more in mass.

As used herein, "removing," "removal," and similar terms mean completely or partially eliminating. For example, removing nitrogen oxides comprises partial or complete biological reduction of the nitrogen in $NO_x$ gases to molecular $N_2$ or other innocuously bound nitrogen as might be fixed in protein or other compounds, thereby either reducing or eliminating $NO_x$, concentrations. Gas means gas, vapor, or air.

Polluted Gases.

For the purposes of the invention, polluted or contaminated gases contain one or more of the following biodegradable polluting gases: nitrogen oxides, which include nitrous oxide ($N_2O$), nitric oxide (NO) and nitrogen dioxide ($NO_2$), generically referred to as $NO_x$; carbon monoxide (CO); sulfur oxides, which include sulfur dioxide ($SO_2$) and sulfur trioxide ($SO_3$), generically referred to as $SO_x$; volatile organic compounds (VOC's) and biodegradable noxious smelling compounds such as from putrescing material, or other undesired gaseous, biodegradable components. Adverse effects of many such compounds is such that emission standards are often set, especially in more prosperous areas of the world. As stated above standards or limits for these compounds' emissions may be specific to such factors as processes, and locations such as US States, districts, or to countries elsewhere.

Nitrogen oxides are a group of common air pollutants, occurring in the atmosphere as a result of both natural processes and processes associated with human activities. Although there are eight recognized nitrogen oxides, three main gases, $NO_2$, $N_2O$ and NO are of most concern. Two, NO and $NO_2$ are air pollutants contributing to the formation of ozone and photochemical reaction products, for which one common term is "smog". Nitrous oxide, although not regarded by regulators as a local air pollutant per se, is nonetheless an extremely potent climate-active "greenhouse" gas of substantial concern as its atmospheric concentrations continue rising worldwide.

Sulfur oxides are also quite common. Sulfur dioxide ($SO_2$) is the most abundant. Sulfur oxides primarily result from combustion of coal and petroleum, with the concentration of sulfur oxides in combustor product gases depending on the initial sulfur content. Like nitrogen oxides, they can have a direct harmful effect once in the atmosphere, as they are toxic to biota and a respiratory irritant to humans. Sulfur oxides can also have a secondary, or indirect harmful effect, by undergoing a common reaction with water in the form of rain or fog to form dilute sulfuric acid, $H_2SO_4$, which along with other acidic compounds often in rainwater, comprises what is termed "acid rain".

A variety of gases are found to be contaminated with these pollutants and are suitable for cleansing by the methods of the invention. Such contaminated gases can result from combustion processes, e.g. exhaust from oil, coal, natural gas, etc. combustion; where the combustion may take place at a factory site, electrical generating site, and the like. Contaminated gases can also result from initial landfill biodegradation processes, where contaminated landfill gas or aeration air is emitted, and also solid waste composting processes which have given rise to numerous odor complaints across the US as reported in the trade literature.

Energies available from pollutant consumption are favorable for the bacteria which carry out pollutant consumption. The pollutant consuming reactions can take place in a variety of reactors, provided there is sufficient aqueous phase containing nutrients, whether nutrients are simple or complex. Reactions by which the desired bioremediation will take place are known in microbiology and the art. Using glucose as the surrogate for the monomer of the cellulose widely present in wastes, some examples of the important reactions and reaction energetics are as follows:

| | |
|---|---|
| Nitrous oxide, $N_2O$ | $12N_2O + C_6H_{12}O_6 \rightarrow 6CO_2 + 6H_2O + 12N_2$ |
| | $\Delta G_o = 81$ kcal/mol $O_2$ consumed |
| Nitric oxide, NO | $12NO + C_6H_{12}O_6 \rightarrow 6CO_2 + 6H_2O + 6N_2$ |
| | $\Delta G_o = 77$ kcal/mol $O_2$ consumed |
| Nitrogen dioxide, $NO_2$ | $6NO_2 + C_6H_{12}O_6 \rightarrow 6CO_2 + 6H_2O + 4N_2$ |
| | $\Delta G_o = 62.4$ kcal/mol $O_2$ consumed |
| ammonia, $NH_3$ | $4NH_3 + 3O_2 \rightarrow 2N_2 + 6H_2O$ |
| | $\Delta G_o = 35.3$ kcal/mol $O_2$ consumed |
| carbon monoxide, CO | $2CO + O_2 \rightarrow 2CO_2$ |
| | $\Delta G_o = 61.5$ kcal/mol $O_2$ consumed |
| Oxidizing gaseous propane (representing a hydrocarbon pollutant) | $C_3H_8 + 5O_2 \rightarrow 3CO_2 + 4H_2O$ $\Delta G_o = 47.6$ kcal/mol $O_2$ consumed |

In general, the Gibbs free energy yield $\Delta G_o$ of these reactions is quite high, ranging from 35 to over 80 kilocalories per gram-atom of oxygen reductively consumed This is whether in reducing oxygen chemically bound in $NO_x$ or used in molecular (gaseous $O_2$) form in oxidizing carbon monoxide, ammonia or hydrocarbons. High free energy is a distinct metabolic advantage for the bacteria in carrying out their microbiological pollutant degradation.

Degradation of sulfur dioxide may occur through the reaction sequence (where standard chemical nomenclature holds and M is a one cation equivalent such as sodium)

$$2SO_2 + 2H_2O \rightarrow 2H_2SO_3$$

$$H_2SO_3 + 2M^+ \rightarrow 2M^+ + SO_3^=$$

and, lastly $$2M^+SO_3^= + \frac{1}{2}O_2 \rightarrow M + 2SO_4$$

Pertinently, the last "sulfite oxidation reaction" oxidizes sulfur dioxide and absorbs oxygen with sufficient rapidity that sulfite solutions' oxygen uptake is used to simulate the oxygen uptake of microbial systems (Augenstein, D. 1967 *Oxygen Transfer in Fermentors at High Power Inputs*. M. S. Thesis, Biochemical Engineering, Course XX, Massachusetts Institute of Technology Cambridge Mass.). The sulfate can also undergo further reactions, but in the end these effectively result in sequestration of the sulfur and preventing emissions of either hydrogen sulfide or sulfur oxide species.

Where the input contaminated gas is exhaust gas, it may require cooling prior to its introduction into the landfill serving as biofilter. It will be evident that in the specific instance of fuel combustor product gas, gas may exit processes at high temperatures, for some exhausts well over 1000° F. Such temperatures are far in excess of the tolerance of the microorganisms likely to be active in consuming pollutants. Thus, for most combustor product gas, precooling will be required to suitably cool temperatures before introduction into any biofilter. A variety of well-documented cooling approaches can reduce the temperatures of the fuel combustor gases as necessary. For example heat exchangers or the ducting of fuel combustor gases through a spray of water will work. Most conveniently, highest fractional energy use of the fuel combustor gas removes much to most of its sensible heat. As an example, the Caterpillar Co. sells combined heated power (CHP) engine-generator sets which realize added sensible heat from the exhaust gas for a variety of purposes such as drying and other process heat (Caterpillar Co.)

Landfill Biofiltration Sections.

Landfills for biofiltration may be of conventional design with minor modifications. Alternately, bioreactor landfills may be preferred. In an anaerobic landfill bioreactor, waste moisture is increased, within constraints of extant federal or other regulations, to speed completion of methane generation and methane recovery to maximum potential. The supplementation may be combined with recirculation of the exit liquid to achieve better distribution and contacting. The relevance of anaerobic operation is that reducing reaction conditions that facilitate methane generation will also facilitate bacterial reduction of $NO_x$, consuming its oxygen and leaving only harmless molecular nitrogen, nitrogen containing proteinaceous material, etc.

In an aerobic landfill bioreactor, air as well as water are introduced into wet waste. One goal of an aerobic bioreactor is to consume organic waste solids by oxidation to $CO_2$ and $H_2O$. In practice this generally occurs in parallel with some anaerobic activity, i.e. decomposition of some of the waste mass to methane and $CO_2$. In the developing aerobic landfill technology, the consumption by oxidation of waste proceeds readily with the addition of water and air (for example see Baker and Johnson (1999) Operational Characteristics and Enhanced Bioreduction of Municipal waste Landfill Mass by a Controlled Aerobic Process. Proceedings, 4th Annual Landfill Symposium, Solid Waste Association of North America, Silver Spring, Md.). A representative reaction for glucose from waste cellulose is $C_6H_{12}O_6 + 6O_2 \rightarrow 6CO_2 + 6H_2O$, $\Delta G_o = 675.6$ kcal or 56 kcal/gram-atom oxygen used. In contrast, the major reaction to produce landfill gas, in wastes yields much less energy: $C_6H_{12}O_6 \rightarrow CH_4 + CO_2 \Delta G_o \approx 33$ kcal/mol $CH_4$ produced.

Even where the energy yield is low, for example in the generation of methane, it is well established to occur in virtually every solid waste landfill tested. Observed landfill gas production clearly indicates presence of conditions permitting biological reactions within nearly all those landfills wherein "landfill gas" is found and produced. Furthermore, the reactions mediating this decomposition of waste, and oxidative biological reactions in general, can be accelerated within the landfill by a factor of at least ten by infiltrating and controlling moisture and operating the landfill as a "bioreactor" (see Augenstein et al. 1998, and Augenstein et al. 2000, supra.)

Methods of Landfill Biofiltration

Landfills potentially provide enormous reaction volume for the desired biofiltration of exhaust gas and other noxious or undesirable components. Landfills also, by nature of typical municipal solid wastes, provide great area upon the surface of the waste per unit volume of the landfill. For example, the surface-to-external volume ratio of a 100 micron diameter paper fiber, or lignaceous remnants of wood pulp such as newsprint, representing examples of waste, and assuming 25-50% voids in situ, will be the order of about 200-400 $cm^2/cm^3$. The surface of waste disposed in a typical landfill can function as a support for the bacteria that mediate desirable pollutant-consuming and contaminant-consuming reactions. Further, landfills already exist, and therefore the cost of setting up a bioreactor need not be incurred.

Landfills therefore have a large capacity for biofiltration. For example, depending on carburetion fuel/air ratio and other factors, a roughly 140,000 $ft^3$/hr volume of exhaust gas may be generated from 1 MWe of electricity generation, which, (using terms often applied to water) is less than 4 "acre-feet of gas". A 10-acre landfill, 60 feet deep, and (for example) 25% voids, could make available as much as 40 hours detention time for the exhaust gas from a 1 Megawatt electric (MWe) engine. And generally, there is even more landfill volume than this readily available at energy use sites.

The technology of bioreactors demonstrates attainability within landfills of circumstances needed to carry out the pollutant biodegradation reactions above. A landfill with proper management of liquid introduction and gas flow will quickly develop high microbial activity necessary for the aerobic degradation of waste. Oxygen is normally present in the fuel combustor exhaust gas at levels well in excess of the microbe's requirement for oxidizing carbon monoxide and VOC's. It will be recognized that the oxidizing landfill waste itself will compete with the VOC, CO and sulfur oxide pollutants for the available oxygen. Where an organic waste remains available to be consumed by oxygen in an aerobic landfill or sectional volume of landfill, competition for oxygen may reduce oxygen in the gas so as to minimize pollutant remediation in the presence of waste oxidation. Competition for oxygen between waste and gaseous pollutant can be minimized by operating the landfill or landfill sector anaerobically until the landfills' oxygen consumption capability can be substantially reduced, and then using that sector of landfill to aerobically degrade pollutants. Alternately, biologically inert components of the landfill such as pea gravel, chip tire, etc., can advantageously serve as zones of oxidative pollutant remediation.

Given this consideration of competition between waste and pollutant for oxygen, the point of initial combustion product gas entry is preferably at a locus in the landfill which has been well oxidized, with organic fractions reducing capacity limited to levels and rates such that oxygen remains available for the desired conversion and consumption of any VOC's, carbon monoxide and sulfur oxides present in polluted gas introduced into the landfill. The gas emitted from the combustion process may lack sufficient oxygen to allow the desired fractional conversion of VOC's carbon monoxide, sulfur oxides, or other pollutant subject to removal by oxidation. This would likely be the case for a combustor having little stoichiometric excess of air. In such systems supplemental air may be added to the stream to be biofiltered.

In an anaerobic bioreactor, reducing conditions are optimized. A mixed microbial flora is capable of generating both intermediates from cellulose, and ultimately methane from the waste (Augenstein, et al. 1998 Yolo County Controlled Landfill Project. Proceedings, Symposium on Landfill Gas Assessment and Management, Ontario, Calif. April available from the California Integrated Waste Management Board, Sacramento; Augenstein et al. (2000), supra.) will contain organisms well-suited for reducing nitrogenous oxides. Organic waste fractions, particularly lignin, remain after initial cellulose degradation, and are expected to comprise 20%-50% of the organics after methane generation has completed. An examination of the stoichiometry reveals that such lignin and other remnant organic wastes have a substantial capacity for the reduction reactions necessary to assimilate the nitrogen oxides.

All of the reactions described above give off heat (enthalpy) of magnitude rather similar to the free energies listed above. The management of heat dissipation is integral to the use of landfill bioreactors. Heat generated by oxidative processes within a bioreactor are of such magnitude that its dissipation may take decades to centuries to be lost from the waste mass if heat loss is by conduction alone (Augenstein (2000b) Bioreactor Landfills—some Engineering Considerations, presented and distributed at Wastecon 2000, Cincinnati, October, Available from SWANA, Silver Spring, Md.). This will hold if oxygen forms over 1% of the polluted gas (including supplemental air) that is to be treated and there is sufficient reducing capacity such as lignin in the waste to consume the oxygen. This heat is most practically removed by adding, or assuring the presence within waste, of supplemental water or aqueous liquid and using the latent heat of water evaporating into the gas stream being treated. The amount of water that must be evaporated for the biofiltration process to function and not "cook to a stop", is about 1.8 grams per kilocalorie generated within the waste or alternately expressed as about 1 pound of water evaporated per 1000 Btu generated by microbial reactions within the waste.

Because the heat of oxidation of most organic compounds may lie between about 35,000 and 85,000 kilogram-calories per kilogram-atom of oxygen consumed in the reaction (as noted above), and conductive losses of heat are essentially negligible on the time scale of pollutant remediation reactions under consideration, the evaporative water consumption can be estimated as ranging between 60 and 200 grams per gram-atom of oxygen consumed ancillary to the gas pollutant biofiltration reaction. The injection of gases and injection or presence of water in the landfill is preferably at a level such as to achieve a temperature of from about 70° to about 180° F. (about 21° to about 82° C.) in the landfill cell. Temperature may be raised (within limits) by increasing air-to-liquid ratio. Temperature may be reduced by reducing the same air-to liquid ratio. However sufficient contacting must also be assured so that fractional oxygen absorption is high; contacting is facilitated by having a large bacterial support surface to volume ratio and long residence time as available in a landfill.

An integral part of the invention is the maintenance of proper moisture levels, neither so low as to limit microbial activity nor so high as to "blind" and shut off pore spaces by filling them with water. Thus, the landfill is preferably maintained at moisture levels between about 20% and about 60% moisture as a weight percentage of wet waste. Based on the water sorption isotherm of cellulose, which can sorb over 5% of its own weight of water in the solid phase, and other considerations including that food masses, mostly moisture, may comprise up to 15% of wet "blobs" relatively ineffective in biofiltration within waste, about 20% moisture level assures that at least some minimal moisture remains as aqueous phase spread over the waste which is acting as support. Values over about 60%, may lead to excessive liquid flows and possible violation of federal constraints on head in the drainage layer over the base liner. One method of attaining a desirable moisture level is by "titrating" waste with water so that water just starts to drain from the bottom of the waste (Augenstein et al., (1998), supra.) Thereafter, makeup water should be added in amount and on schedule as needed to make up for evaporative losses. The pH is maintained sufficient to facilitate further microbiological reactions. The pH of liquids within well-maintained anaerobic and aerobic landfills may be maintained in the most desirable ranges of 6 to 8.5 by adding acid or base or buffers as necessary.

Waste will contain an abundance of organisms including those capable of metabolizing nearly all or all the "usual" solid waste components. In startup, however, the organisms necessary for consuming pollutants identified above could likely to be present in fairly small numbers in the waste. This is because waste does not normally contain these pollutants. In the moist waste, exposure to gaseous contaminant compounds enables growth of necessary bacteria to levels that allow oxidation of these compounds. In startup, in order that the pollutant degrading organisms increase as much as possible without undesirable emissions levels, the process generating the gaseous pollutants may begin at a slow rate. If, for example, the biofiltration substrate is an internal combustion engine's exhaust, the engine may be started at part load. As exit gas analyses begin to show desirable fractional removals of pollutants, the magnitude of engine output, or other pollutant producing process may be increased. It is worth noting that with a typical microbial doubling time of 4 hours, a desired increase in organisms of, e.g. $10^6$ fold would take only about 80 hours. Once the waste microbial culture has developed to the point enabling pollutant removal, the experience with aerobic landfills suggests intermittent "start-stop" operation should be straightforward.

The degree of pollutant abatement will be of concern in many cases, both to regulators and others. If the sole input of gas to the landfill is an air-fuel combustor exhaust, the degree of abatement can be assessed by measuring the normalized concentration of the pollutant of concern against atmospheric nitrogen in combustor exhaust using standard means for gas analysis (e.g., gas chromatography, and the like). If both combustor exhaust, and air to facilitate oxidative processes are introduced into the waste, a material balance can be attained and contaminant reduction can be assessed relative to a low-cost low-level tracer such as helium or sulfur hexafluoride carefully metered into the combustor exhaust. An integrated surface scan can give much of the needed data; however maximum accuracy in determination of fractional contaminant abatement from exit gas composition is attained by collecting or combining most or all exit gas in a single stream.

Methods for the transport of gases into a landfill are known in the art, and are readily adapted from the prior art transport of oxygen or air, to the transport of contaminated gases as taught by the present invention. The contaminated gases, as previously described, may be the product of combustion, e.g. exhaust from factories and energy generation, or noxious or odorous gases as evolved during certain phases of waste composting.

In general, modes of gas introduction and withdrawal shown effective for aerobic landfilling, as it is known to those skilled in the art, will also serve for the oxidative pollutant consumption reactions of the present invention. For most effective pollutant removal, a "plug flow" residence time distribution in which gas elements take as close-to-equal amounts of time as possible to pass through above waste zones will be the most effective. The residence time or residence time distribution (the time range of fastest to slowest passage of gas through the landfill) preferably lies within limits such that the pollutants are biologically abated to the desired degree with a single pass. The landfill design must be such as to duct gas with the desired residence time distribution through the waste. This will not only require gas inputs and outputs as indicated, for example, in FIGS. 1-3 but also the degree of containment of the waste margins (top, bottom and sides) to confine gas flows to prevent exit of too much "fugitive" untreated gas or "short circuiting". If porous solid waste base or cover layers can allow short circuits, these can be of high area/volume support material already commonly used to construct such layers in landfills, e.g. sand, pea gravel, etc., which can accomplish biofiltration.

The specific design of the apparatus for the injection of air and water into the landfill to promote the aerobic composting reaction will vary with the specific requirements of the landfill. The general design can include the venting of depleted air and water vapor at the top of the landfill and the venting of depleted air, water vapor and leachate at the bottom, e.g. with a series of perforated pipes in roughly planar and near-level form conforming to the top and bottom of the landfill. The pipes are spaced depending on the mass and void volume of the waste section to be utilized for biofiltration. The piping system may be valved so that different parts of the cell can be treated with greater or lesser flows in order to accommodate variations in bioremediation abilities of those different parts of the cells. The flow programming of the injection into the landfill can be based on the measurement of temperature in the cell, and on the oxygen/carbon dioxide and any remnant pollutant content of the off gas from the cell.

A grid of gas injection wells may be established throughout the landfill. The landfill's gas injection system can comprise gas stream blowers or pumps that are connected to an existing leachate collection system cleanout ports, which are typically located along the sides of a landfill. Areas that can filter and receive more contaminated gas as the system operates are augmented by additional contaminated gas supply through the vertical gas injection. The gas header or duct piping may be corrugated plastic agricultural drainage pipe if high flexibility and load resistance are needed. Vertical gas wells may be made of plastic (Polyvinyl chloride (PVC) being often used), or metal pipe set at appropriate intervals throughout the waste. Or, wells may simply be flow channels of highly porous material (such as gravel or shred tires) of high permeability relative to waste as described in Augenstein et. al. (1998), supra. As polluted gas is forced into inlet ports or introduction surfaces, or the leachate collection system, and into the waste, the gas distribution system is pressurized and managed so that the gas travels outwardly through the piping slotting (or screened casing) and upward through the waste mass with maximum possible uniformity, that is, all elements of introduced gas spend times within the waste that are as similar as possible. Alternatively, vertical wells consisting of standard well component materials, and which may have external casing, or screens, are installed vertically into the waste mass and connected together via a common header system (piping). Using the wells, pollutant-contaminated gas may be either introduced into the waste or pulled through the waste from the gas's introduction points elsewhere. Blowers connect to provide gas to the header system and to the vertical wells, or vacuum from identical blowers may pull gas from the waste when it is introduced elsewhere into the header system and thence to exhaust. The important feature of any of the possible arrangements for pollutant-contaminated gas introduction and withdrawal is that it assure at minimum a gas residence and waste contact time that is adequate for required pollutant bioremediation.

An additional feature of the invention is that heats generated by reactions need to be dealt with so that highly exothermic energy yielding reactions, as described above, do not cause the bioremediation to "cook to a stop" or evaporate water in the waste to the point where waste is "dried to inactivity". Calculations show that conduction of heat away from the waste mass will in most cases be unacceptably slow. Practical and necessary heat loss rates are assured by presence or addition, and subsequent evaporation into the gas stream of sufficient moisture so that the liquid's or aqueous amendment's latent heat of evaporation carries away the heat generated by oxidative biological or other exothermic reactions occurring in the waste. The wells for introducing polluted-gas or multiple purpose gas addition/extraction wells are installed into waste and operated, and moisture assured added, via approaches as well-known in the art. Examples of such moisture addition methods are described (Augenstein et al. (1998), supra.; Pacey et al. (1999), supra.) Normal, natural precipitation may also comprise a part of the water component. Aqueous amendments serve to provide the necessary supplemental moisture to evaporatively dissipate heat generated by oxidative reactions in the landfill. Other described moisture addition methods will work providing distribution is achieved.

The gas flow rate and liquid flow rates are adjusted by either adjusting or throttling gas and liquid wells, selectively isolating gas or liquid wells through valving, thereby shutting off or increasing gas or liquid to selected areas as needed. One very useful option is to follow, adjust and assure moisture distribution through use of in-waste moisture and temperature sensors (Augenstein et al., (1998), supra.) The moisture sensors have been demonstrated to show clearly the key moisture profile in the waste. Temperature sensors provide an indication of the reaction rates and exotherm in vicinity of the sensors. Temperature-humidity readings of gas slightly beneath or at the surface of the waste will also indicate levels of desired biological activity in the waste elements beneath the zone where readings are taken. Another operational option, where gas and particularly oxygen transfer may be a rate-limiting step, is adjustment (lengthening) of polluted gas residence time to allow sufficient oxygen consumption, thence heat generation, and thence water vapor partial pressure and evaporation so that all oxygen is consumed and anaerobiosis, where necessary, is achieved. Finally, tracers may be used as an aid in determining reaction progress and material balance as discussed later.

FIG. 1 shows schematically one embodiment of the invention. The fuel in FIG. 1 is "landfill gas" extracted from an appropriately active gas-generating section of a landfill. The landfill is comprised of a waste sector 30, and may further comprise one or more sectors of degraded waste 25. The anaerobic section of the landfill is shown to be shaded, and the aerobic section is unshaded. The landfill may be situated above a porous base layer 35, and be covered with suitable waste cover layers 10, which may include a membrane cover 15. A permeable gas extraction layer 20 may also be present. The fuel combustor is an engine 1 operated on landfill gas 2 extracted from a sector of the landfill which is still actively producing methane. The engine exhaust gas is ducted through a cooling section 3 where gas is cooled by means well-known to the art, e.g. water spray, heat exchange, etc. to cool the gas, realize benefits of additional exhaust heat, and the like. The gas is cooled to below 300° F., preferably down to its dew point to minimize (in the case of the normal excess-oxygen combustors) any danger of fire or pyrolytic product formation. Added introduced air flow may be needed to evaporatively dissipate heat, or allow full oxidation and bioremediation of pollutants or both. In such cases air is added to provide at least that necessary excess of said oxygen-containing gas to allow oxidation of the CO, VOC's and SOx in the landfill. Alternately, the necessary criterion may be that the air addition is sufficient to allow the necessary evaporation to dissipate the heats of reaction.

Figure 2:
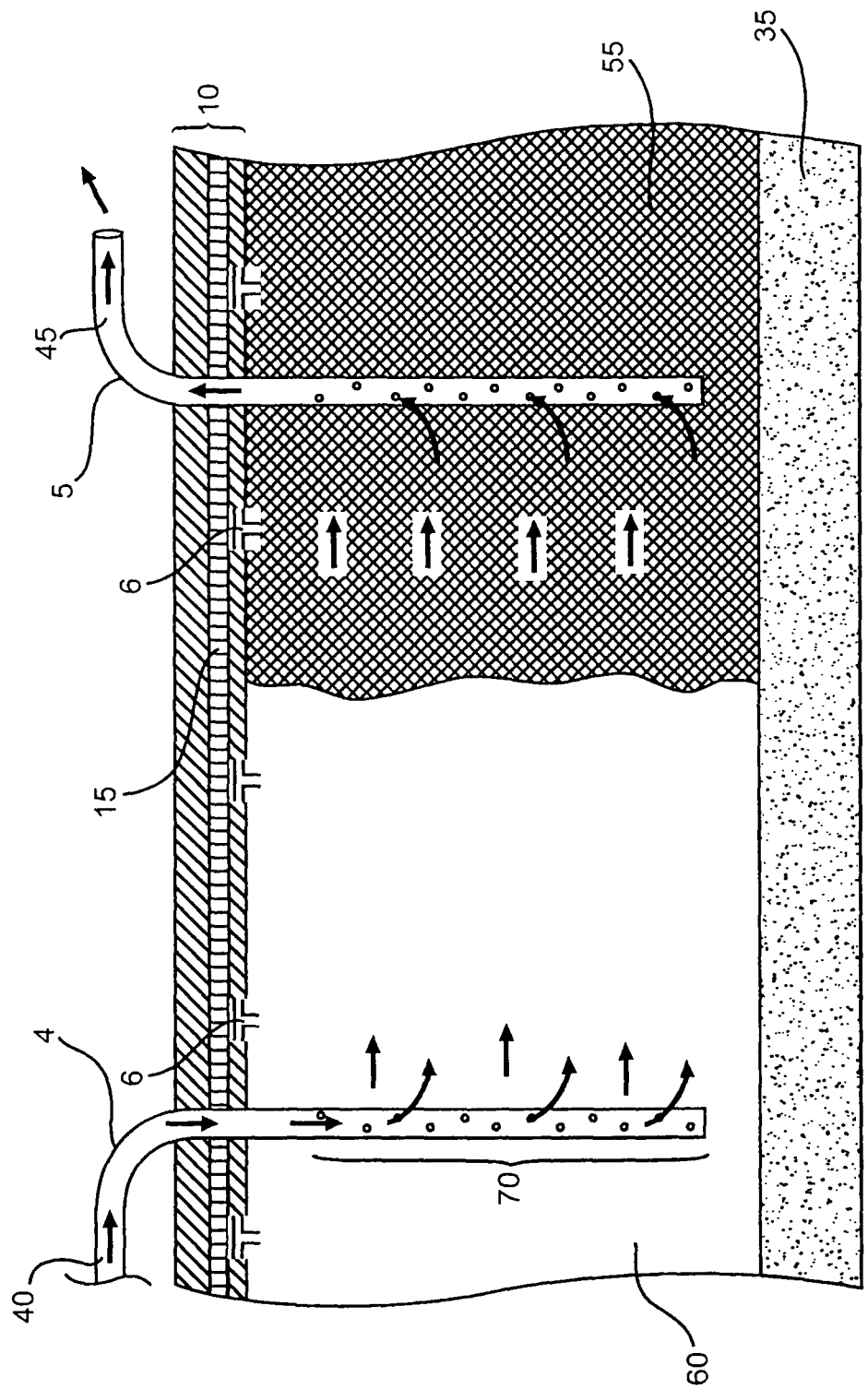
FIG. 2 is a schematic of a landfill biofiltration system utilizing vertical wells for injection and withdrawal.

FIG. 2 shows one arrangement of wells demonstrated as workable for gas (oxygen from atmospheric air) transfer. Vertical wells 4 and 5 are used for introduction of contaminated gas 40 and extraction of clean gas 45, respectively. Any moisture essential to permit reaction is added through inlet(s) represented by 6. The vertical wells have a perforated zone 70 for flow of gas. Although only one gas introduction well 4 and one gas withdrawal well 5 is shown in FIG. 2, there may be a multiplicity of gas introduction and withdrawal wells operating in tandem so as to accomplish the necessary gas contaminant bioremediation. The aerobic zone of the landfill 25 is depicted as unshaded 60, while the reducing zone ($O_2$ absent) is depicted as shaded 55. The base layers 35, which may be gas-conducting, and gas-conducting cover may also be of substrates such as sand or gravel upon which bioremediation can take place. The whole of the landfill area wherein bioremediation occurs may also have low-permeability cover, which may be the common low permeability clays, or, for example, geomembrane above a porous surface layer. Liquid is added as appropriate at locations at the surface (shown by 6 in FIG. 2) or within the waste.

Figure 3:
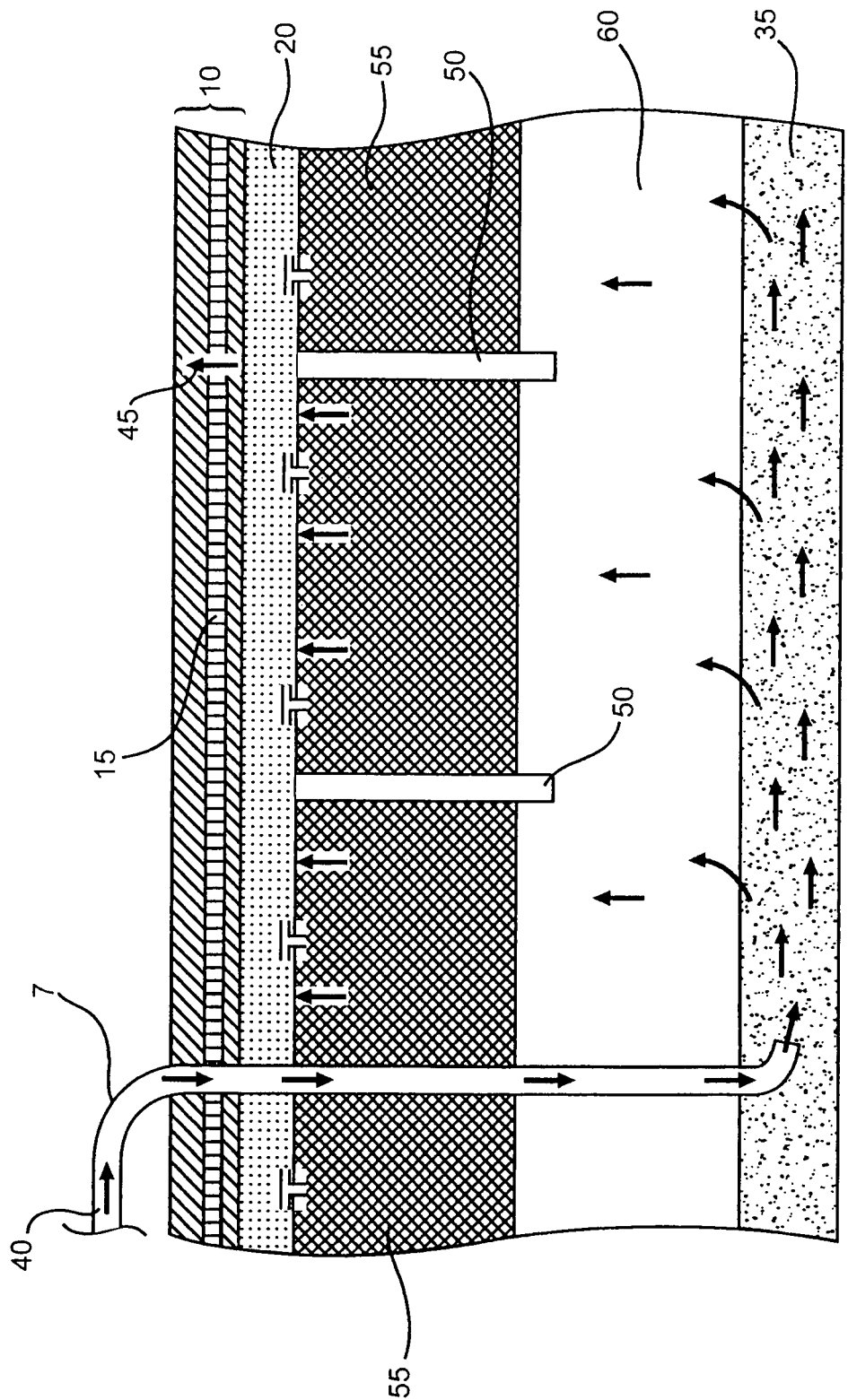
FIG. 3 is a schematic of a landfill biofiltration system utilizing the landfill base layer for introduction of polluted gases, and, if desired, surficial layers for gas withdrawal.

FIG. 3 shows an alternative arrangement, in which the fuel combustor or other contaminated product gas passes vertically upward through the waste using a permeable base layer as a zone of gas introduction. As in FIGS. 1 and 2, the reducing zones 55 and 60 are shown by shading. In this embodiment, the input gas 40 is input through a gas inlet line 7 and the clean, biofiltered gas 45 is then released to the atmosphere via a permeable gas extraction layer 20. Wells 50 would normally be present in a degraded landfill but are not required for the present invention, and are shown for completeness only.

As gas is ducted (pumped) or drawn into the aerobic and thence anaerobic zones of the landfill it can be expected, at the first startup, that necessary organisms may need to be allowed time to grow to necessary levels. In the aerobic zone, the gas from the aerobic zone of the bioreactor will necessarily be slowly depleted of some amount of its oxygen ($O_2$), by reaction with the pollutant materials (VOC's, CO, and the like) and also by reaction of $O_2$ with remnant landfilled waste organics. Once oxidizable pollutants and oxygen are removed, normal progress of the gas stream will be to an anaerobic zone, in which reducing organics such as lignin remain. The conditions in the anaerobic zone (expected to be the majority of the landfill) favors the consumption of the nitrogenous oxides.

"Channeling" or "short circuiting" may occur, such as to limit bioremediation of some fraction of gaseous pollutants. In this phenomenon, gas might flow through preferred channels within waste, without necessary gas-to-waste contacting to achieve desired bioremediation. For such conditions, channeling may be detected by introducing with the contaminated gas, easily quantified non-reactive gaseous tracers not ordinarily present in the interstitial gas within the waste. One such gas is helium, and another, sulfur hexafluoride, however many nonreactive gases available, particularly noble gases, can suffice. The value of these tracers is that timing or their emission and zones of their emission may be detected, as well as degrees of remediation. When problems are detected, gas flow can be shut off to areas where gas channeling is occurring, with consequent redirection through areas of active bioremediation.

What is claimed is:

1. A method for removing biodegradable gaseous pollutants from contaminated gases, the method comprising:
    permeating said contaminated gases into a 1000 ton or more tonnage landfill waste mass, wherein said gaseous pollutants comprise nitrogen oxides, including one or more of nitrous oxide (N20), nitric oxide (NO) and nitrogen dioxide (NO2); and
    maintaining said waste mass such that microorganisms present in said waste mass biodegrade said gaseous pollutants to substantially reduce said nitrogen oxides to N2;
    wherein the contaminated gases are exhaust gases from combustion of landfill gas,
    in which zones, rates and percentages of contaminant reduction by bioremediation are assessed and thence controlled by means relying on localization, at points in or above the waste, of gas contaminant concentrations relative to known inert gas or inert gas tracer inputs.

2. A method for removing biodegradable gaseous pollutants from contaminated gases, the method comprising:
    permeating said contaminated gases into a 1000 ton or more tonnage landfill waste mass, wherein said gaseous pollutants comprise nitrogen oxides, including one or more of nitrous oxide (N20), nitric oxide (NO) and nitrogen dioxide (NO2); and
    maintaining said waste mass such that microorganisms present in said waste mass biodegrade said gaseous pollutants to substantially reduce said nitrogen oxides to N2;
    wherein the contaminated gases are exhaust gases from combustion of landfill gas,
    in which the overall degree of biofiltration is assessed by contaminant reduction measurement relative to known inert gas or inert gas tracer inputs at a single gas outlet location where all gas exiting the biofiltration is commingled and well mixed.

* * * * *